United States Patent

Blecher et al.

Patent Number: 5,395,347
Date of Patent: Mar. 7, 1995

[54] SAFE BLOOD COLLECTION SYSTEM

[75] Inventors: Jacob B. Blecher, Lexington; Miles C. O'Donnell, Andover; William McCormick, Carlisle, all of Mass.

[73] Assignee: MBO Laboratories, Inc., North Chelmsford, Mass.

[21] Appl. No.: 972,013

[22] Filed: Nov. 6, 1992

Related U.S. Application Data

[63] Continuation-in-part of Ser. No. 610,583, Nov. 8, 1990, Pat. No. 5,176,655.

[51] Int. Cl.⁶ ............................................. A61M 5/32
[52] U.S. Cl. .................................. 604/198; 604/192; 128/766
[58] Field of Search ............... 604/162, 167, 192, 198, 604/263, 197, 195, 110; 128/760, 765, 766, 919

[56] References Cited

U.S. PATENT DOCUMENTS

| | | |
|---|---|---|
| 4,935,012 | 6/1990 | Magre et al. |
| 4,946,446 | 8/1990 | Vadher ................................ 604/198 |
| 4,998,924 | 3/1991 | Ranford .............................. 604/198 |
| 5,026,356 | 6/1991 | Smith .................................. 604/192 |
| 5,122,121 | 6/1992 | Sos et al. ............................ 604/167 |

FOREIGN PATENT DOCUMENTS

| | | |
|---|---|---|
| 0281421 | 9/1988 | European Pat. Off. |
| 3808688 | 3/1987 | Germany |
| 3807388 | 10/1988 | WIPO |
| 8807387 | 10/1988 | WIPO |
| 8904183 | 5/1989 | WIPO |
| 8910767 | 11/1989 | WIPO |
| 9000075 | 1/1990 | WIPO |
| 9101151 | 7/1991 | WIPO |

Primary Examiner—C. Fred Rosenbaum
Assistant Examiner—V. Alexander
Attorney, Agent, or Firm—Low and Low

[57] ABSTRACT

A safety needle and blood collection and sampling system precluding needlstick injury by contaminated needles wherein a used needle is captured immediately within its carrier upon retraction of the needle flush with the carrier. Blood sampling is effected without reverse flow through the system and without reuse or exposure of a contaminated needle. Simplified techniques of assembling the needle are also set forth to minimize cost with maximum reliability notwithstanding a minimum of components.

20 Claims, 8 Drawing Sheets

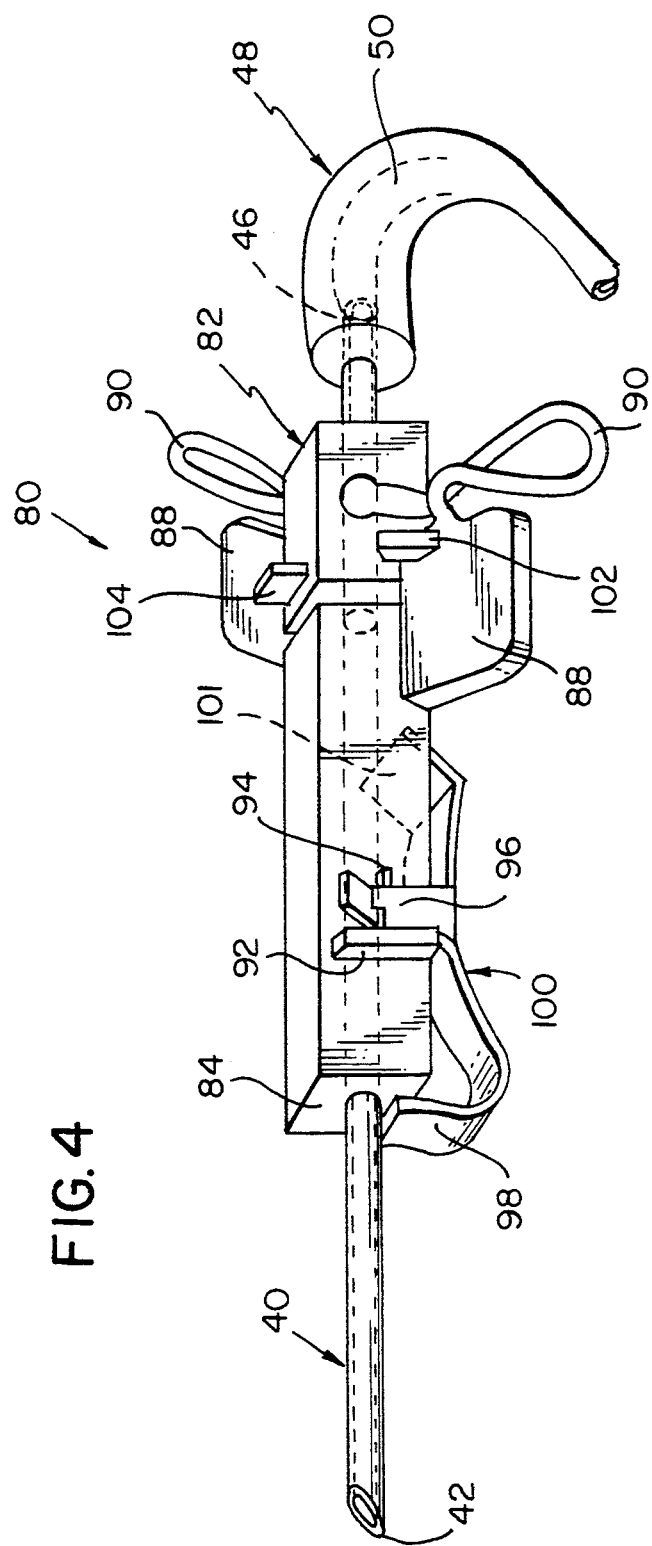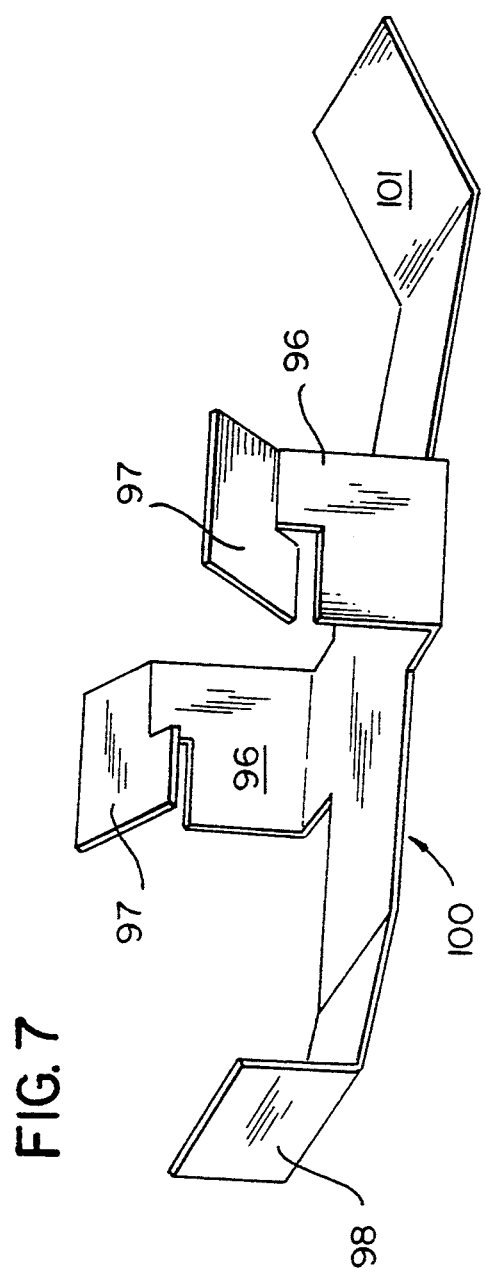

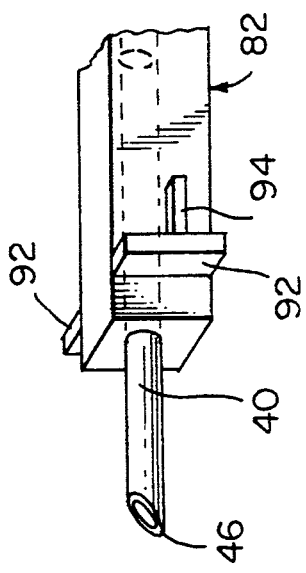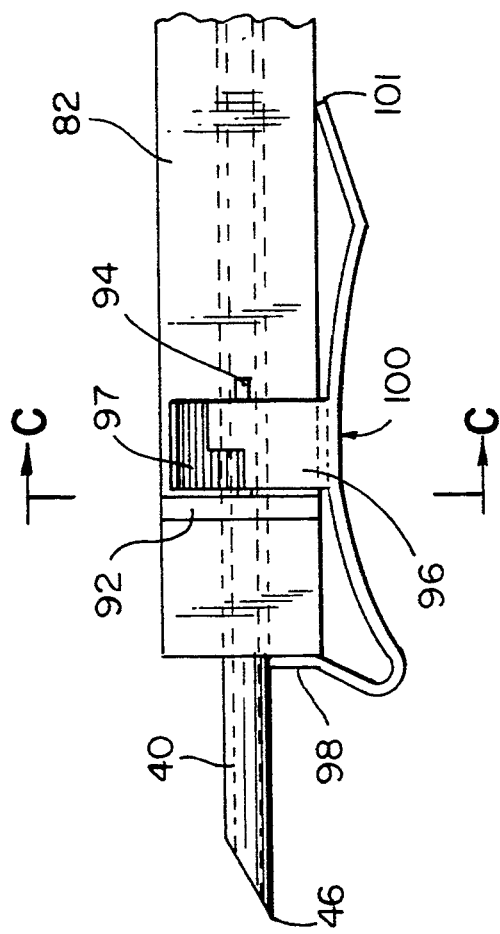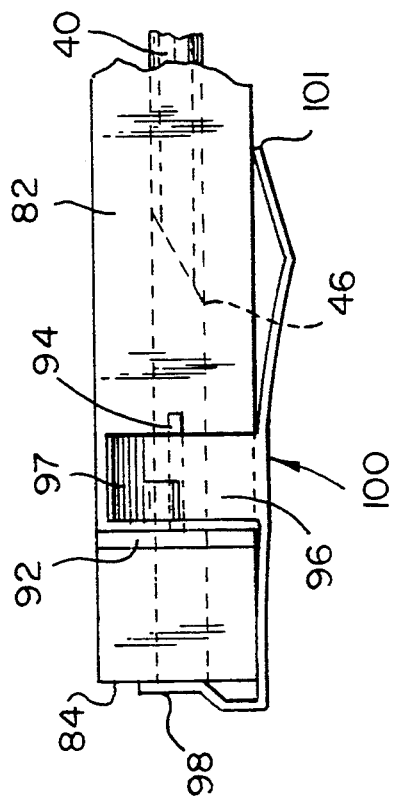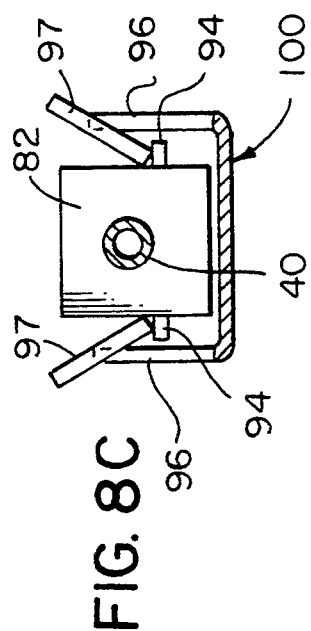

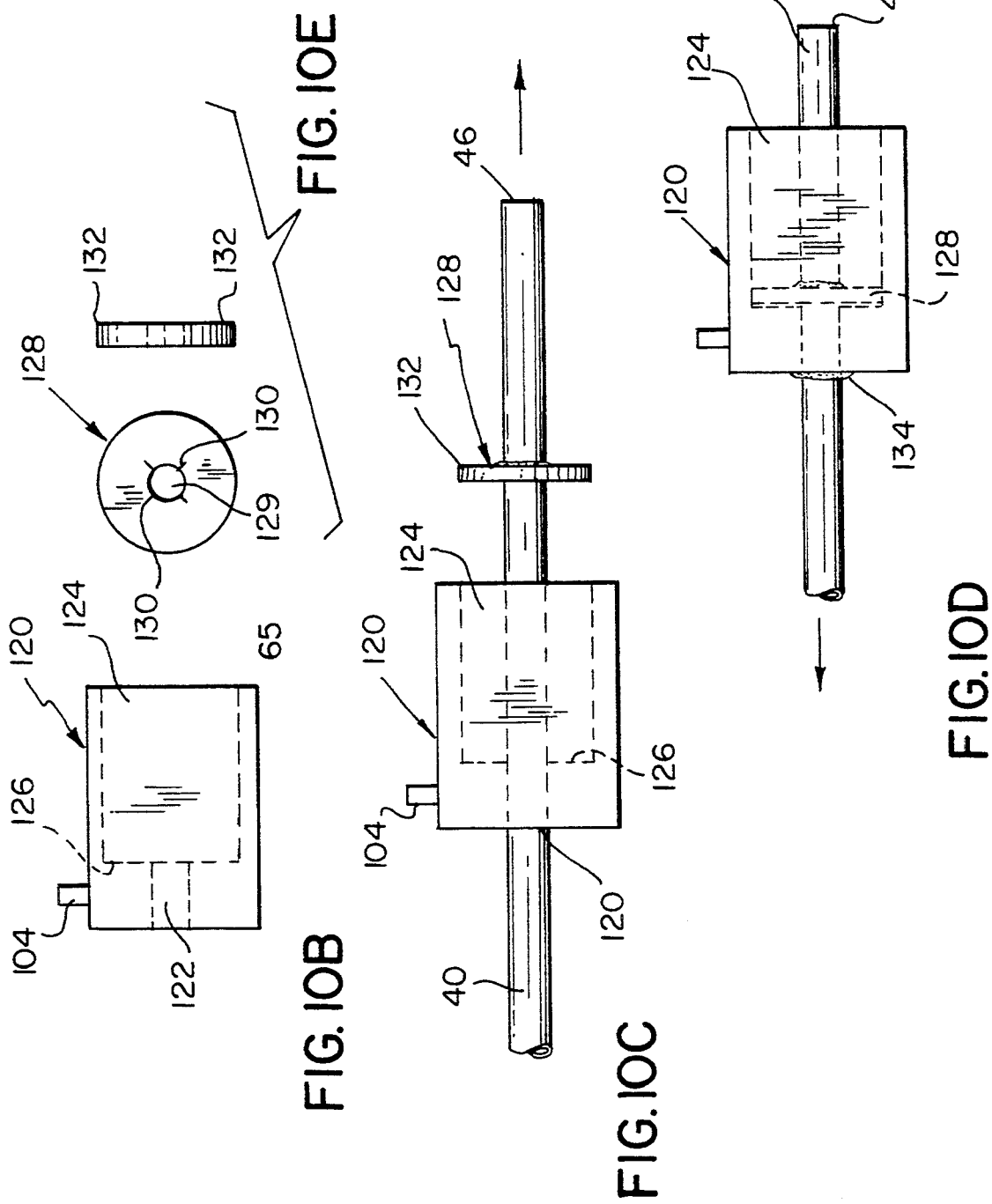

SAFE BLOOD COLLECTION SYSTEM

CROSS-REFERENCE TO RELATED APPLICATIONS

This application is a continuation-in-part of our pending application Ser. No. 07/610,583 filed Nov. 8, 1990, now U.S. Pat. No. 5,176,655, issued Jan. 5, 1993, and is also a continuation-in-part of our pending application PCT/US91/08063 filed Nov. 6, 1991 under the Patent Cooperation Treaty.

BACKGROUND OF THE INVENTION

At high-volume medical facilities as blood bank centers, hospitals, and the like, blood is drawn from human donors in large quantities for processing and storage. In connection therewith, small volume specimens of the blood are withdrawn from the blood collection apparatus for necessary analysis. Blood withdrawal from humans exposes the medical worker to the risk of accidental needlestick injuries preparatory to connection of blood collection equipment to the donor in the unavoidable handling of used, unshielded, blood-contaminated needles.

In current practice, blood banking services, such as the American Red Cross among others, obtain, process, and store whole blood and blood components for a variety of medical uses such as transfusions and the like. Before any such blood can be used, however, all collected blood is analyzed to characterize its immune properties or so-called "blood type". Equally or more importantly, all blood must also be pre-tested for the presence of communicable disease pathogens, such as the hepatitis virus and the human immunodeficiency virus (HIV). As is well known, HIV is the causative agent of the uniformly fatal AIDS disease in humans, and thereby mandates the safest possible environment when handling human blood.

Blood collection as now commonly practiced utilizes a system including (1) a straight metal needle whose pointed end is inserted into a human donor to access a blood vessel wherein the needle usually includes a gripping portion bonded thereto to facilitate manual manipulation; (2) a length of flexible tubing in fluid communication at one end with the non-pointed proximal end of the needle; and, (3) one or more blood storage bags connected to the other end of the tubing. Additionally, helpful agents such as citrate-phosphate dextrose (CPD) are commonly included as anti-clotting additives within the collection system to prevent coagulation of the blood and permit it to remain in fluid condition.

Accordingly, traditional blood bag collection apparatus is thus a closed, sterile system in which the blood flows from the donor's blood vessel through the tubular metal needle, through the flexible tubing and into the blood storage bag, and in the use thereof for actual blood collection does not present a significant hazard to medical personnel.

As indicated, however, it is necessary to take a small sample of collected blood for analysis to insure the integrity and quality of the bag quantity. Customarily, to obtain the test sample, the medical or health care worker initially shuts off tubing flow as by a clamp, and then grips the needle with one hand by the enlarged grasping component thereof, removing the needle from the donor. Thereafter, the exposed needle tip, which is now blood-contaminated, is inserted through a rubber stopper or seal into a sample collection test tube, and the clamp is released to permit drawing of a sample of the collected blood reversely through the needle and into the test tube usually held in the other hand.

The open manipulation of the contaminated needle between withdrawal and sample securement presents unwanted hazards to personnel in the possibility of accidental needlestick injury.

Thus, the physical movement of the contaminated needle with one hand toward and in close proximity to the other hand holding the sample collector, there is a significant probability of self-inflicted injury. In effecting the sampling, the needle point may misalign with the rubber seal and puncture the worker's hand. Additionally, upon withdrawal of the inserted needle from the sample vial, the frictional resistance of the rubber stopper retarding needle withdrawal suddenly ceases as the needle pulls clear, and there is an involuntary tendency and reflex for the worker's hand holding the needle to recoil back toward the hand holding the test tube.

The actual rates and likelihood of needlestick injuries with such conventional blood collecting equipment have been well documented in a report appearing in the publication *TRANSFUSIONS*, Vol. 29, No. 8, October, 1989, pages 693–695, entitled "Needlestick Injuries in Blood Collection Staff—A Retrospective Analysis". Attempts to improve the present practice by using a guard mechanism to reduce the chances of accidentally puncturing the healthcare worker's fingers, especially those grasping the sample tube, have reduced but failed to eliminate the rates of such injuries. In one typical Red Cross blood collection center, for example, there are about 10 to 12 needlestick injuries annually out of a total staff of 165 individuals who are in fact using such a prior art guard device.

There is, therefore, a substantial and real need for means to eliminate the needlestick hazard and its actual threat to the health of medical workers in blood collection operations.

Concomitant to the foregoing, ease of fabrication, simplicity of assembly, and reliability of function are prime requisites of devices and equipment in the healthcare arts. To this end, the present invention embraces improved and reliable needle-carrying and manipulating elements, and modes of fabrication and assembly thereof.

SUMMARY OF THE INVENTION

The present invention addresses this problem confronting the healthcare industry and is designed specifically to eliminate needlestick injuries of the type described in connection with blood collection.

To this end, there is provided a new and improved system which (1) shields the blood-contaminated needle simultaneously with its withdrawal from the donor, and (2) uses a separate shielded needle in a blood sample tube holder for the safe drawing of blood samples, whereby the probability of an exposed contaminated point being in any injury-causing proximity to a medical worker is virtually nil, whereby the threat to or even the fear of HIV or other disease by the worker is eliminated.

To this end, a unique and mechanically simple but reliable snap-on needle enclosing guard is provided on a specialized needle device disclosed herein, which is similar in some respects to the needle safety device as set forth in our aforenoted copending application Ser.

No. 07/610,583. Thereby, upon withdrawal of the needle from the blood donor, the needle is immediately retracted within the guard and a shield positively blocks the contaminated needle point and access thereto. Two different forms of the needle assembly are provided and which have differing fabrication and use advantages.

Obviously, such protection precludes use of the same needle for the aforementioned separate sampling purposes. The invention, therefore, further embraces means to effect the necessary sampling without the use of a contaminated needle and without concomitant needlestick exposure of the worker.

BRIEF DESCRIPTION OF THE DRAWINGS

The invention will be better understood in reference to the accompanying drawings in which:

FIG. 4 is similar to FIG. 3 showing the apparatus with advance of the needle for insertion into the donor;

FIG. 7 is a perspective view of the shield spring member;

FIG. 8A is a view of the end of the guard with the needle extended therefrom, but with the shield removed for clarity;

FIG. 8B is an enlarged side elevation similar to FIG. 8A but with the shield in initial position;

FIG. 8C is a view taken on the line C—C of FIG. 8B;

FIG. 8D is a fragmentary view similar to FIG. 8B but with the needle retracted and shielded;

FIG. 10B is a side view of the modified gripping member, internal portions being shown in phantom;

FIG. 10C is a partial assembly view of a needle and its securing disc with the moified gripping member;

FIG. 10D is an assembled view of the parts of FIG. 10C; and,

FIG. 10E are front and side views of the needle securing disc.

DESCRIPTION OF THE PREFERRED EMBODIMENTS

Figure 1:
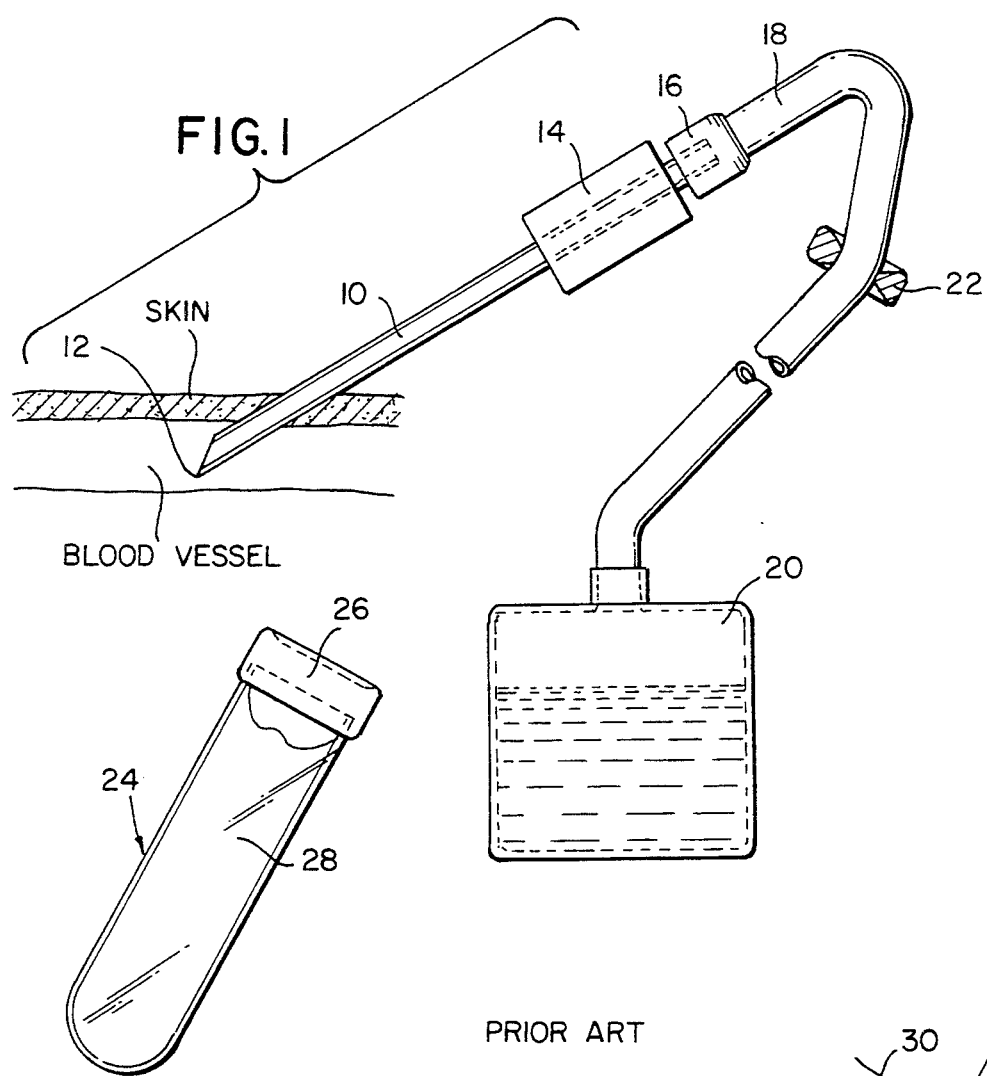
FIG. 1 is a diagrammatic illustration of prior art presently practiced blood collection technique and equipment.
Figure 2:
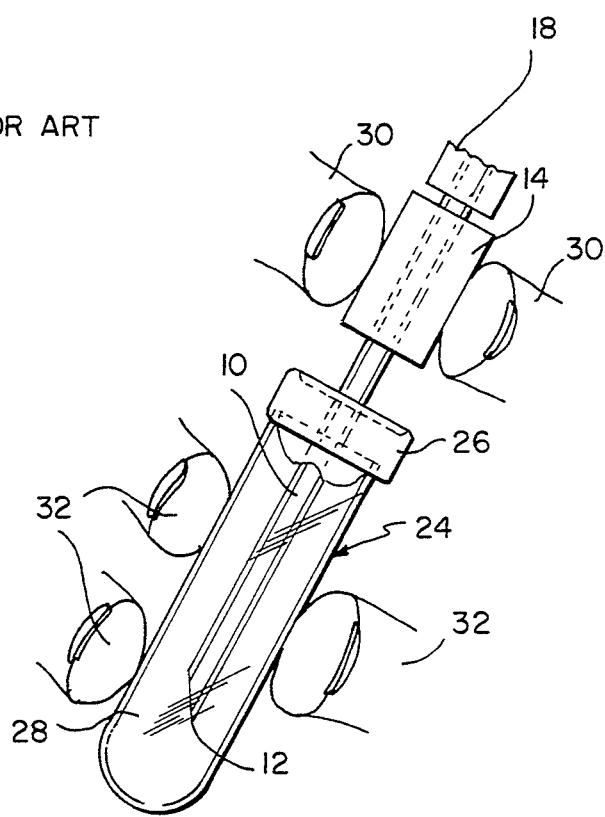
FIG. 2 is an illustration of prior art sample collection in a test tube.

Referring to the drawings, there is generally indicated in FIGS. 1 and 2 a typical widely used blood collection and blood banking system which in use presents the aforementioned safety and needlestick hazards. Thus, a hollow metal cannula needle 10 having a tapered point 12 has a finger-grippable enlarged annulus 14 secured to a proximal needle portion to facilitate handling and maneuvering of the needle in the collection and sampling process.

The donor's skin is punctured by the point 12 and the same is the positioned in a blood vessel. The proximal end 16 of the needle is bonded, clamped, or otherwise secured in known manner to flexible tubing 18, the opposite end of which communicates with a blood collection bag 20, whereby the needle, tubing, and bag form a closed passageway for the flow of blood. Clamp means 22 of known form is provided along tubing 18 to regulate or shut off blood flow as may be required from time to time during collection or thereafter.

There is also provided a standard blood specimen tube 24 having a usual rubber seal stopper 26. Such sealed tubes are conventionally provided on manufacture with an partial vacuum in its internal chamber 28 to facilitate the drawing of blood thereinto. Such specimen tubes 24 are routinely used for taking small volume blood samples for analysis from donor blood obtained for blood bank processing and storage purposes.

The current practice of obtaining the blood samples entails a procedure which is in fact hazardous to health care workers. After the desired quantity of blood is collected from the donor into bag 20, clamp 22 is used to shut off flow. The fingers 30 of one hand of the worker grasp enlarged collar 14 and remove needle 10 from the donor and move the now-contaminated needle point 12 through space to aim and position the point 12 to puncture stopper seal 26 of the specimen tube 24, the latter being held by fingers 32 of the other hand of the worker, as seen in FIG. 2. The clamp 22 is released, and a small quantity of blood is drawn in reverse flow from the tubing 18 into the partially evacuated chamber 28 in specimen tube 24.

Apart from other real possibilities of mishandling the contaminated needle tip 12 during donor withdrawal and holding the same openly as the specimen tube is manually positioned, it is principally the manipulation of needle 10 for alignment and entry into specimen test tube 24 that constitutes a significant danger of accidental needlestick injury to the health care worker. In necessarily moving a blood-contaminated needle in one hand directly toward the other hand holding the tube, and with sufficient moving force to penetrate the stopper 26, the danger of self-inflicted injury increases substantially. Thus, the needle point 12 may miss the small-diameter stopper entirely and puncture the fingers 32. Alternatively, the needle point may be improperly positioned at an angle on the stopper 26 and with stopper-puncturing force applied, the needle may slip laterally from the stopper and puncture the worker's hand. These possibilities are entirely apart from other imperfections of the worker as relatively poor eyesight, nervousness, and the like.

Additionally, as earlier noted, there exists the threat of injury in retracting the needle from the vial stopper 26 from a recoil-like motion immediately after the needle 10 is pulled out of stopper 26 and the previously existing frictional resistance of the rubber to needle withdrawal suddenly ceases. As the blood-contaminated needle then starts to "fly" rearwardly on leaving the stopper, there is a frequent immediate reflex by the worker to stop the rearward motion and abruptly move the needle again toward the fingers 32 holding the specimen tube with risk of scratching these fingers with the needle.

These difficulties are obviated by the apparatus and system of FIGS. 3-9. Thus, therein, the blood-contaminated needle is shielded simultaneously with its withdrawal from the donor whereby no inadvertent puncture can occur, and a separate shielded needle in a blood sample tube holder is used for safe drawing of the blood sample.

Figure 3:
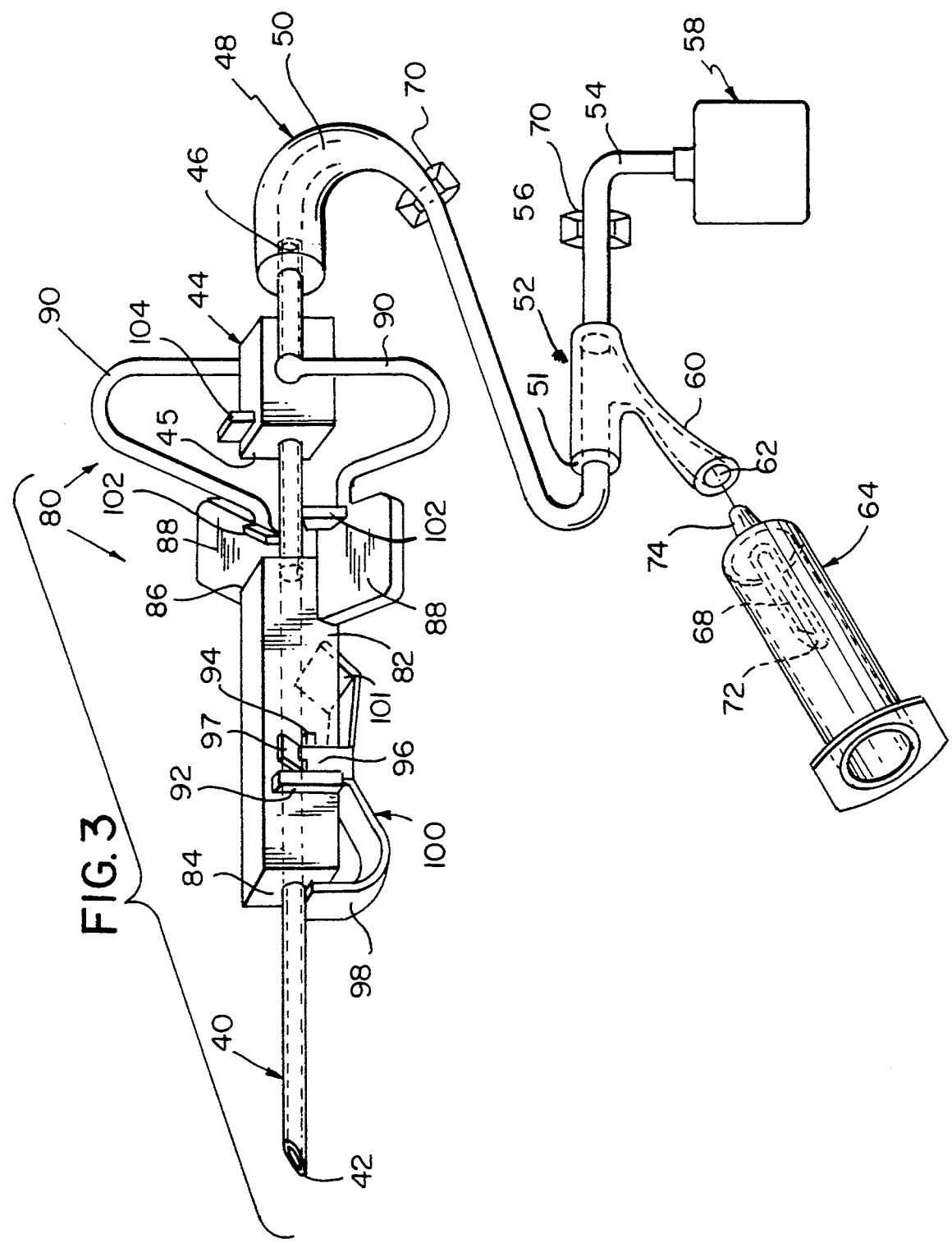
FIG. 3 is an overall perspective view of the blood collection system of the invention.

One form of the invention is seen in FIG. 3 wherein needle cannula 40, somewhat similarly to needle 10 in FIG. 1, includes the usual needle point 42 and further includes a special gripping portion or base member 44 bonded therearound near the needle proximal end 46, which latter is secured in usual manner to the flexible blood collection tubing 48 having its internal flow passage 50. Tubing 48 terminates into one branch end 51 of a Y-connector 52 of well-known form, while a length of tubing 54 extends from the other end 56 of the Y-fitting 52 to communicate with blood bag 58. Well-known flow control adjustable clamps 70, 70 are provided along the length of tubing 48 and 54.

The Y-fitting includes a second branch 60 providing a sampling port 62 communicating with the tubing 48. The port 62 is a conventional medical industry fitting, commonly known as a Luer female fitting. The port 62 is adapted to cooperate with a standard blood collection tube holder 64 having a standard multiple sample blood collection needle 68 with a rubber sleeve 72 associated with a male Luer fitting 74, which latter forms a dripless collection with female port 62. Prior to sample collection into tube holder 64, the fitting 74 is inserted into the port 62 to prevent drippage until the collection tube is inserted into holder 64 in known manner to open access to needle 68.

The safety and guard assembly 80 in FIGS. 3 and 4 carrying needle 40 in overall respects is in accordance with that disclosed and claimed in our copending application. The same includes a needle guide body 82 having an opening shown as a bore extending from distal end 84 to proximal end 86 within which needle 40 is slidably received. While the body 82 is shown for illustrative purposes as being of square or rectangular cross-section, the particular configuration may vary within the limits of the required structure and function thereof. Similarly, the assembly may readily be fabricated as by molding from plastic, such as polyethylene, polyvinyl chloride, or the like.

The rear portion of front guide 82 may be provided with laterally extending flexible winglike members 88, and flexible restraints or tethers 90 extending from wings 88 interconnect the guide 82 and the base section 44 which is bonded to needle 40. In the absence of wings 88, the tethers 90 may be connected directly to the body 82. The wings 88 also include respective upstanding lugs 102, 102 outwardly from the guide body 82 for cooperation in use with an upstanding lug 104 on base section 44, as described further hereinafter.

Preferably, needle guide 82 is provided on either side thereof with a series of laterally extending projections 92 and 94 for cooperative abutment with gripping legs 96 of a specially configured leaf spring 100. Obviously, the spring legs 96 could cooperate with other forms of abutments than protrusions, as recesses in the guide body 82, for example.

The spring 100 forms an essential element of the safety needle assembly. Thus, as shown in FIG. 3, the spring includes an inturned flange 98 at its forward end, which rests upon and is biased transversely against needle 40 when the needle is extended for use as shown.

The proximal end 101 of spring 100 is also angled and stressed against the guide 82, the spring being maintained in position by the inwardly angled portions 97 of legs 96 bearing against projections 94.

Uniquely, the one-piece spring 100 facilitates assembly of the unit, as the inwardly angled portions 97 of legs 96 thereof readily snap past the body flanges 94, and positively hold the spring on the body with no chance or accidental removal. The assembly is thus a one-step process minimizing cost with no sacrifice of safety or reliability. As above noted, the protrusions 94 may be replaced by molded indentations in the body 82 with equally effective results. The forward or vertical protrusions 92 preclude any likelihood that the spring could slide forwardly on the body to expose excessively the needle, while the safety flange obviously precludes rearward movement of the spring.

Accordingly, the needle assembly 80 comprises the needle 40, the front guide 82 slidably carrying the needle, the flexible tethers 90, the rearmost base section 44 bonded to the needle, and the spring 100.

Figure 5:
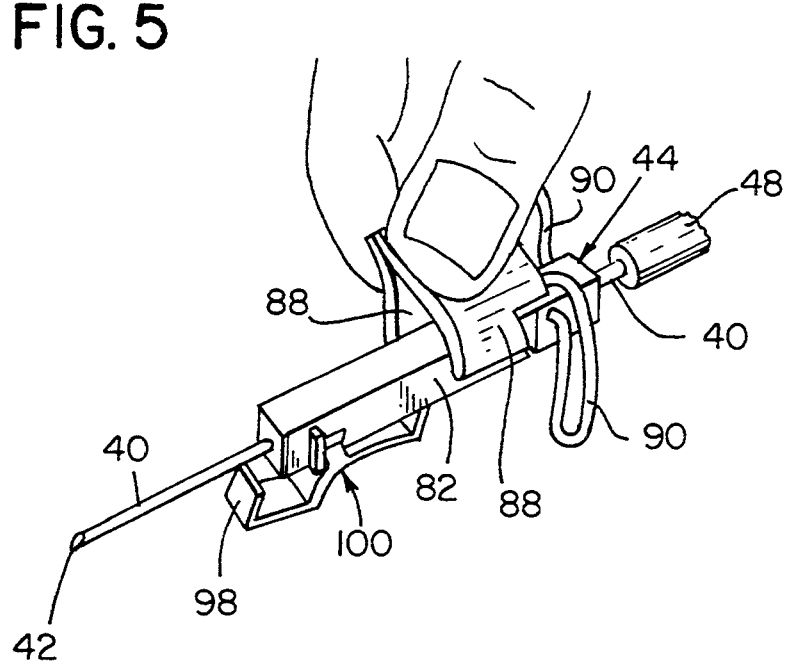
FIG. 5 is an illustration of the gripping means of the apparatus for needle insertion.
Figure 5A:
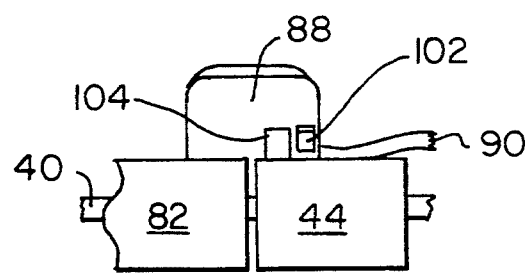
FIG. 5A is a fragmentary side elevation of the device as seen in FIG. 5.

In use, and as set forth in applicants' copending application, now U.S. Pat. No. 5,176,655 during preparation for needle insertion through the skin of the blood donor, the assembly 80 is as shown in FIG. 4 with the wings 88 initially flexed sufficiently downwardly to permit base section 44 to closely approach or abut the forward needle guide 82 from the former position of FIG. 3. Thereupon, the wings 88 are flexed upwardly and gripped as seen in FIG. 5. In so doing, the wing lugs 102 are repositioned to be disposed immediately rearwardly of the base member lug 104 as best seen in FIG. 5a. Thereupon, with forward movement by the fingers gripping wings 88, base member will move forwardly therewith to insert the needle point into the donor.

While the foregoing is a positive and unitary handling of the assembly 80 during needle insertion, under particular conditions with a donor or patient, the medical technician may leave the wings down and separately manipulate the base member 44 and the needle carried thereby to insert the needle without concomitant interlocked or interengaged lugs 102, 104.

Figure 6A:
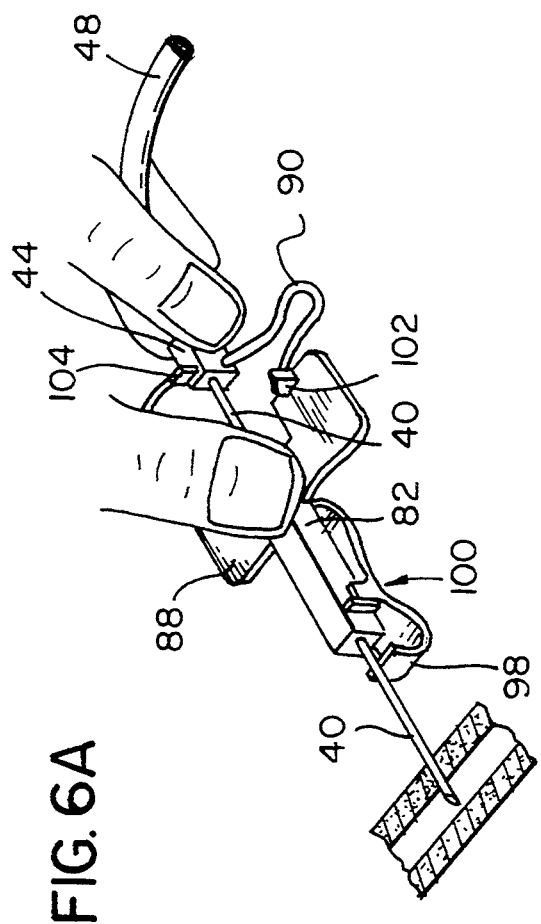
FIG. 6A is an illustration of the system at commencement of needle withdrawal from the donor.

As similarly taught in Ser. No. 07/610,583, now U.S. Pat. No. 5,176,655 safe needle withdrawal from the donor's (or patient's) blood vessel is effected by holding the guide member or front section 82 stationary adjacent the needle skin entry point and with wings 88 relaxed to remove lugs 102 outwardly from behind lug 104. Thereupon, as shown in FIG. 6A, the base section 44 (or the tubing 48 thereat) is pulled in a proximal direction while needle guide 82 is stationary thereby causing needle 40 to slide rearwardly in the proximal direction through the guideway therefor in guide 82.

Figure 6B:
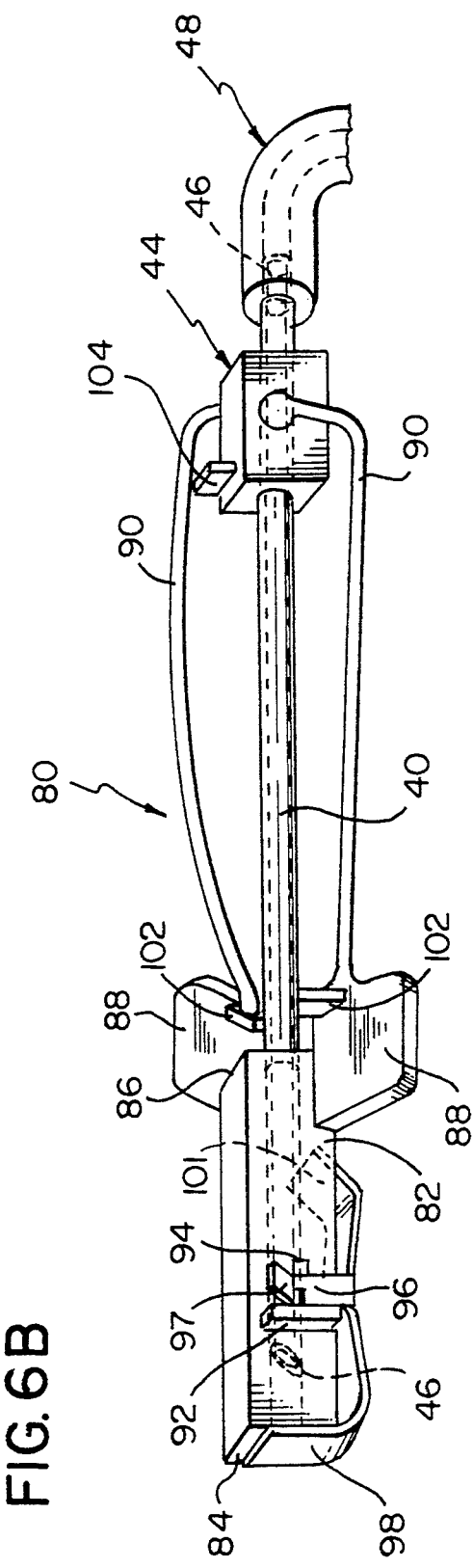
FIG. 6B illustrates full withdrawal of the needle and enclosure thereof with in the guard and protection of the needle point by the shield.

Thus, with the construction described, immediately as the needlepoint passes rearwardly of the distal end of spring 100, the spring relaxes and snaps the angled face 98 thereof transversely of the guide and securely encloses the needlepoint within guide 82 as seen in FIG. 6B. It should be borne in mind that as compared to the drawing illustrations, the actual device of the invention is quite small, and the needlepoint is absolutely without capability of exposure and contact with medical or donor personnel once retracted and blocked, whereby needlestick injury is positively prevented in a simple and effective manner.

More particularly, and this is an outstanding safety feature of the invention, with the spring angle face 98 immediately adjacent the end of the body at 84, as soon as the needle passes behind the face 98, the spring snaps over the end 84 of the body and positively precludes reemergence of the contaminated needle point from the body 82 and thus needlestick injury is absolutely avoided. While the needle may be withdrawn further into the body 82, such extra movement is unnecessary as the safety spring acts on and over the end face 84 of the body at the immediate point of potential emergence of the contaminated needle. The fully withdrawn and safety-shielded needle is shown in FIG. 6B, for example.

This contrasts with other attempts to reduce injury wherein the needle must be withdrawn at least a minimum predetermined distance beyond the exit from the tubular body. With such equipment, a visual perusal indicates that the needle is not exposed, and therefore may be considered to be safe. In fact, if the needle is not retracted sufficiently inwardly from the exit aperture, it is still able to be accidentally projected to cause hazard, and is not securely in a safe position immediately upon its retraction inside the carrying body, with no further retraction being required. Such devices are known in the prior art.

Figure 9A:
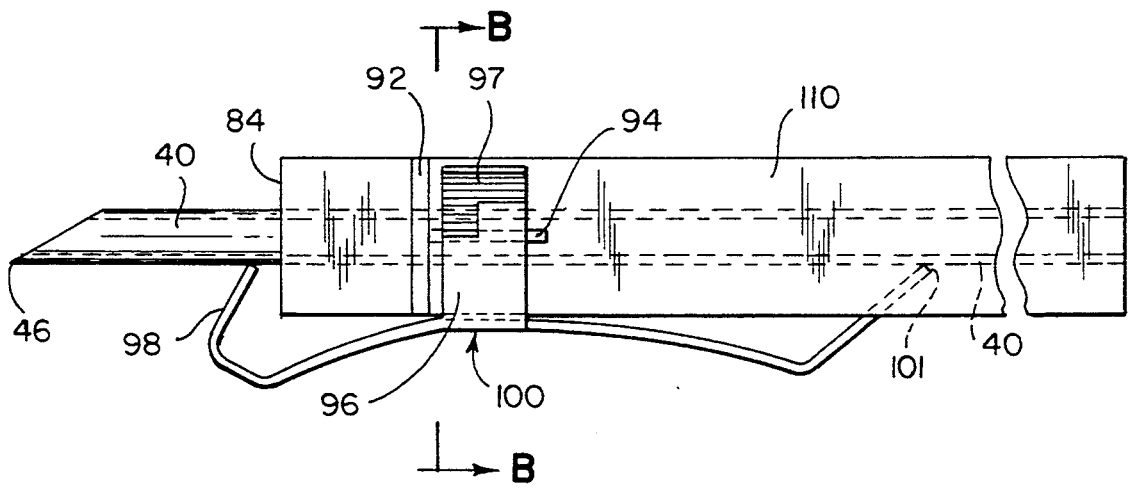
FIG. 9A is a view similar to FIG. 8B illustrating a modified needle carrier and guard.
Figure 9B:
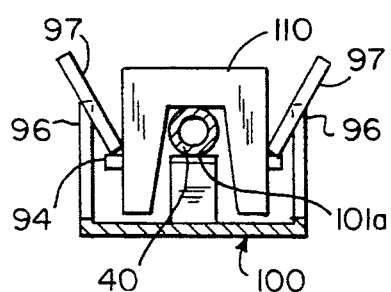
FIG. 9B is a view taken on the line C—C of FIG. 9A.
Figure 9C:
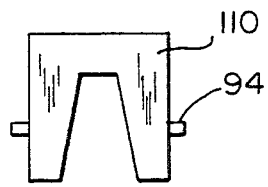
FIG. 9C is a section view similar to FIG. 9B but with the shield and needle removed.
Figure 10A:
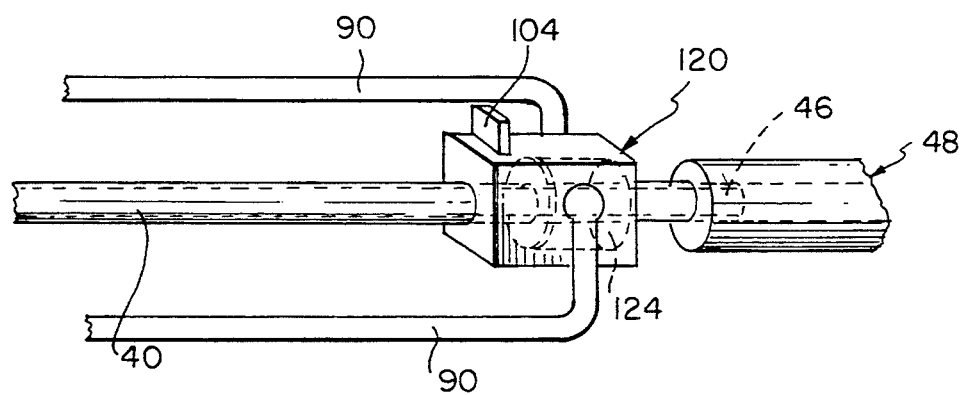
FIG. 10A is a view similar to FIG. 6B but showing a modified form of gripping portion for the needle.

A modified body 110 for receiving the needle is shown in FIGS. 9A–C in lieu of the body 82. The same is not provided with a tubular bore as in FIG. 3, but with an open-sided U- or V-configuration. as well seen in FIG. 9B. In so doing, the spring 100 has a modified rear tang 101a dimensioned to fit within the body 110 and bear against the needle 40 therein. Along with the forward safety shield 98 of the spring, the needle is held firmly in the body, and upon snap operation of shield 98 as heretofore, the needle is safetied, being blocked at its proximal end, gripped at 101a, and overlaid by the body generally of the spring, whereby access cannot be had to the needle point. In other respects the elements of the assembly 80 are essentially the same. It will be evident that the U-shaped body facilitates ready assembly of the needle system.

FIGS. 10A–10E illustrate a modified form of gripping member and a simplified assembly technique for associating the needle 40 therewith. Thus, the modified gripping element 120 is similar to that at 44 in FIG. 3 in being of polymeric material and generally of cylindrical or polygonal external configuration and includes a similar upstanding wing-engaging flange 104. Internally thereof, however, instead of a simple through bore as in FIG. 3 for receiving and bonding as by cement to the needle 40, only a short needle-diameter bore portion 122 is provided in the distal end thereof, the member 120 being countersunk therebehind to an enlarged diameter chamber 124 having an internal front wall 126.

Cooperating therewith is needle-gripping and securing disc 128 having a diameter substantially that of chamber 124, and having a hole or aperture 129 therethrough bounded by short radial cuts 130. Hole 129 is of a diameter slightly less than that of the needle 40 whereby the cuts 130 permit slight flexing of the disc as the needle is inserted therethrough in a snug mechanical interference fit.

Additionally, disc 128, which is preferably fabricated from thin flexible metal, is provided at its periphery with a plurality of rearwardly directed barbs or tangs 132. Accordingly, the disc is assembled with gripping member 120 by axially advancing the disc into chamber 124 against front wall 126, and is locked therein by the presence of the barbs 132 whereby the disc cannot be removed and the needle is securely positioned. Further, a liquid bonding agent is applied about the needle at 134 (FIG. 10D) at its exit from member 120, thereby sealing the needle to the base gripping member 120.

In this manner the needle is reliably secured to the member 120 both by the mechanical interaction of the disc 128 with base 120 and also by the bonding material 134.

Accordingly, in summary, It will be seen that in use with cannula 40 inserted into the patient, blood is collected into bag 58 as desired, and then the clamp 70 is shut and the needle 68 opened onto a collection tube for desired sampling without removal of the needle 40 from the patient. As many samples may be taken as desired with manipulation of the clamps 70, 70 prior to retraction and immediate safetying of the needle 40 without reuse thereof or hazard therefrom. The healthcare worker at no time has to manipulate an unshielded blood-contaminated needle whether collecting blood or taking samples for analysis.

The assembly of the present invention lends itself to ready fabrication, as is evident from the foregoing. Thus, the body 82, gripping portion 44, tethers 90 and wings 88 if used may be simultaneously molded, as by injection molding, of polymeric material, as polyvinyl chloride. The unit assembly may then have the needle 40 appropriately positioned in the body 82 and the gripping portion 44 for bonding of the distal needle portion to member 44. If the modified U-body 110 of FIG. 9 is employed, the needle need not necessarily be prepositioned therein, but all elements other than member 44 can be flexed to one side while the needle is fixed to 44. In either case, thereafter the spring 100 is snap-fitted onto the body, and the assembly is complete and ready to use. The same advantages in assembly accrue with the needle securement technique of FIGS. 10 A–D, as above discussed.

While we have disclosed our invention in preferred embodiments, it is evident that the concepts and techniques thereof may be employed in differing arrangements, such as indwelling needles, tubing, biological fluid reservoir, drainage systems for pleural fluid drainage, and the like, within the scope of the invention as defined in the appended claims.

What we claim is:

1. A safety needle and safe blood collection system comprising:

a needle having a distal portion terminating in a pointed end and a proximal end, a body having means for receiving the needle for sliding movement therein and, said body having a front surface through which the needle distal portion may be extended by sliding movement from said body and retracted into said body, and, movable safety means cooperatively associated with said needle and said body for permitting movement in only one direction for blocking immediately and positively reemergence of said needle distal portion through said body front surface immediately upon retraction of the point of said needle to a position flush with and overlying said body front surface, thereby retaining said needle distal portion within said body with no portion thereof extending or projecting outwardly from said body, said safety means having a configuration for precluding reversing movement in the opposite direction thereof to a position permitting reemergence of said needle distal portion from said body, said safety means including an imperforate blocking flange disposed in adjacent relation to said body front surface when said needle is extended therefrom, and spring means for urging said flange into adjacent overlying relation to said body front surface upon retraction of said needle into said body, whereby a used needle cannot have its point or adjacent distal portion reexposed for hazard and injury after initial retraction thereof into said body.

2. The safety needle and blood collection system of claim 1 wherein said urging means presses said flange against said needle whenever said needle is projected from said body whereby upon immediate clearance of said needle point from said flange when said needle is retracted therepast permits said flange to immediately cover said body front surface to block reemergence of said needle.

3. The safety needle and blood collection system of claim 2 wherein said body includes a tubular bore for receiving said needle.

4. The safety needle and blood collection system of claim 2 wherein said needle-receiving body front surface has a length greater than that of said safety means imperforate flange,
whereby when said flange covers the body front surface and thereby the needle retracted in the body, said flange cannot be inadvertently or accidentally flexed in a reverse direction to expose the needle.

5. The safety needle and blood collection system of claim 2 wherein said body includes a U-shaped channel along the length thereof in which said needle slides, said channel having an open side.

6. The safety needle and blood collection system of claim 5 wherein said urging means includes a portion thereof extending along said channel on the open side thereof to preclude lateral movement of said needle outwardly from said channel.

7. The safety needle and blood collection system of claim 1 further including a blood collection bag, a sample tube holder, a three port fitting having ports respectively connected to said bag and said holder, and a length of flexible tubing connected between said proximal needle end blood collection fitting and a port of said three port fitting.

8. The safety needle and blood collection system of claim 1 including means mounting said spring means on said body, wherein said mounting means include abutment means on said body, and spring legs on said spring lockably interengageable with said abutment means.

9. The safety needle and blood collection system of claim 1 further including a grippable base member affixed to the needle adjacent its proximal end and including a bore through which the needle extends, said base member having front and rear ends, and said needle projecting outwardly therefrom on both said ends thereof.

10. The safety needle and blood collection system of claim 9 wherein said base member is provided with an enlarged chamber extending inwardly from one end thereof, and means in said chamber for gripping said needle.

11. The safety needle and blood collection system of claim 10 wherein said gripping means includes an apertured disk mechanically gripping said needle.

12. The safety needle and blood collection system of claim 11 further including bonding material extending between said needle and said base member.

13. The safety needle and blood collection system of claim 9 further including a standard tubular blood connection fitting at the proximal end of said needle.

14. The safety needle and blood collection system of claim 13 wherein said standard blood connection fitting is a male fitting.

15. The safety needle and blood collection system of claim 13 wherein said standard fitting blood connection is a female luer fitting.

16. The safety needle and blood collection system of claim 1 wherein said safety means is a one piece metallic spring.

17. A method of withdrawal of the safety needle of the system of claim 1 from flesh into which it has been inserted to prevent needlestick hazard therefrom comprising the steps of:
causing the terminal end of the spring-urged imperforate flange safety means to bear against the side of the needle while said needle is inserted into the flesh,
holding the front surface of the body carrying the needle closely adjacent the flesh at the locale of needle insertion,
sliding the distal end of the needle rearwardly through the body while the body is held in position,
so withdrawing the needle from the flesh until the needle distal portion is within the body and the pointed needle end is withdrawn from the flesh and from bearing engagement with the safety means, and is substantially flush with the front surface of the body,
immediately capturing the needle distal portion and pointed end within the body by spring-urged movement of the safety means flange over the front surface of the body to a rest position blocking the needle, and,
preventing reversible movement of the safety means from the rest position by the configuration thereof so as to prevent positively reemergence of the contaminated needle from the body.

18. The method of claim 17 including the further step of providing the safety means imperforate flange with a length less than that of the front surface of the body,
whereby upon the safety means attaining the rest position blocking the needle, the terminal end of the flange does not extend beyond the body front surface and thereby cannot be inadvertently or accidentally flexed in a reverse direction to expose the needle.

19. The method of fabricating a safety needle system comprising the steps of:
providing an elongated needle,
providing a carrier for slidably receiving the needle therein, with said carrier having a U-configuration to define an elongated groove for receiving the needle and open to one side, and a front surface through which the needle extends,
providing a spring including a front flange,
affixing said spring to said carrier to dispose said spring flange in spring-urged pressing relation against said needle immediately adjacent said carrier front surface, and further mounting said spring to block said carrier open side, thereby to prevent needle dislodgement from said groove,
whereby upon slidable retraction of said needle into said carrier to a position flush with said carrier front surface, said flange is spring pressed to move in front of said surface and block needle movement therepast.

20. The method of fabricating a safety needle system comprising the steps of:

provided an elongated needle, providing a carrier for slidably receiving the needle therein, with said carrier having a front surface through which the needle extends and may be retracted, providing a one-piece metallic spring including an imperforate front blocking flange and laterally disposed resilient legs having gripping surfaces, affixing the spring to said carrier for movement in only one direction by snapping the resilient legs over and against either side of the carrier to dispose said imperforate flange in spring-urged pressing relation against the needle immediately adjacent said carrier front surface with the spring under tension, whereby upon slidable retraction of the needle to a position flush with the carrier front surface, the imperforate flange is spring pressed to move in front of said surface and block sliding needle movement from the carrier therepast.

* * * * *